United States Patent [19]

Lemole

[11] Patent Number: 5,554,173

[45] Date of Patent: Sep. 10, 1996

[54] DEFIBRILLATOR CHARGE TESTER

[76] Inventor: Gerald M. Lemole, 404 Tomlinson Rd., Huntingdon Valley, Pa. 19006

[21] Appl. No.: 323,470

[22] Filed: Oct. 13, 1994

[51] Int. Cl.$^6$ .............................. A61N 1/00; A61N 1/08; G01R 1/06; G01R 31/12

[52] U.S. Cl. .................................... 607/1; 607/5; 607/27; 324/149; 324/548; 324/550; 324/690

[58] Field of Search .............................. 607/1, 5, 27, 29; 324/437, 548, 550, 557, 149, 690

[56] References Cited

U.S. PATENT DOCUMENTS

| | | | |
|---|---|---|---|
| 1,636,707 | 3/1924 | Robinson et al. | 324/548 |
| 2,023,916 | 6/1933 | Dante | 324/550 |
| 2,290,760 | 5/1940 | Mehaffie | 324/149 |
| 3,389,703 | 6/1968 | Criswell et al. | 607/142 |
| 4,105,968 | 8/1978 | Mobley et al. | 324/149 |

FOREIGN PATENT DOCUMENTS

| | | | |
|---|---|---|---|
| 1185240 | 3/1970 | United Kingdom | 324/690 |

OTHER PUBLICATIONS

Thomas, Harry E. *Handbook of Biomedical Instrumentation and Measurement,* Chapter 3—Cardiac Emergency Equipment—The Defibrillator, Reston Publishing Company, Inc., A Prentice–Hall Company, Reston, VA, 1974, 66–77.

*Primary Examiner*—William E. Kamm
*Assistant Examiner*—Carl H. Layno
*Attorney, Agent, or Firm*—Seidel Gonda Lavorgna & Monaco, P.C.

[57] ABSTRACT

A defibrillator charge tester includes a generally fork-shaped nonconductive shell defining two prongs and a handle. A charge testing circuit is disposed in the shell. The circuit terminates at two ends. A conductive plate-shaped contact member is disposed at each of the two ends, external to the shell. In use, the contact members touch respective defibrillator electrode surfaces. The circuit includes a fuse to prevent reuse of the tester.

15 Claims, 9 Drawing Sheets

DEFIBRILLATOR CHARGE TESTER

FIELD OF THE INVENTION

This invention relates to a testing device for verifying whether an appropriate charge exists on a defibrillator electrode.

BACKGROUND OF THE INVENTION

The defibrillator is a physiotherapy instrument that discharges a capacitor through the chest of the patient (external defibrillation) or directly through the expired heart (internal defibrillation) to bring the random activity of the fibrillating heart to a standstill and allow the organ to resume its normal rhythmic pulsations. The capacitor is discharged through a pair of external paddle electrodes placed against the patient's chest or a pair of internal electrode paddles placed directly on the heart. To sufficiently shock the patient's heart and return it to its normal rhythm, discharge voltages as high as several thousand volts are employed.

U.S. Pat. No. 3,389,703 discloses a defibrillator electrode suitable for performing defibrillation. The electrode comprises a shallow circular dish with a handle extending therefrom. The surface of the dish which contacts the patient is convex. Smaller versions of electrodes similar to the one shown in U.S. Pat. No. 3,389,703 have flat contact surfaces. Other types of defibrillator electrodes have disk-like shapes and radially attached insulated handles.

It is extremely important that the defibrillator be checked to ensure that it is functioning properly before the electrodes are placed on the patient and the capacitor is discharged. The wires connecting the defibrillator to the electrodes are typically constructed of carbon fiber which are prone to breakage. Currently, a defibrillator charge tester is employed to detect that the electrodes are charged.

FIGS. 1, 2 and 4 shows one such prior art charge tester and FIGS. 3 and 5 illustrates how it is employed. FIG. 1 is a top perspective view of the entire tester and FIG. 4 is a bottom perspective view of a portion of the tester. FIG. 2 shows the charge testing circuit disposed inside the tester. FIG. 3 is a perspective view showing how the tester contacts the defibrillator electrodes and FIG. 5 is a sectional view showing the tester/electrode contact.

FIG. 1 is a top perspective view of the prior art tester 100. The tester 100 consists of a generally Y-shaped flattened nonconductive hollow plastic shell 101. The Y-shaped shell 101 is defined by identical tines or prongs 102, 104 and a handle portion 106. Each prong 102 and 104 has a rounded distal end 108 and a proximal end 110. A pointed conductive pin or contact member 112 extends from the distal ends 108 of each of the prongs 102 and 104. The handle portion 106 includes ridges 114 for assisting the operator in gripping the tester 100. The mid-section of the top side of handle portion 106 has a cut-out covered by a translucent window 116. The contact members 112 actually extend through the shell 101 and thus terminate inside of the shell 101, as best shown in prior art FIG. 2.

FIG. 2 shows charge testing circuit 118 superimposed over the tester 100 with the components of the testing circuit 118 in their approximate locations with respect to the parts of the shell 101. It should be understood that all portions of the testing circuit 118, except for the protruding portion of the contact members 112, are disposed inside the shell 101.

The testing circuit 118 is a series connected path consisting of the two contact members 112, a resistor 120 and a lamp 122. One end of the resistor 120 is connected by wire 124 to the contact member 112 associated with the prong 104. The other end of the resistor is connected to one terminal end of the lamp 122. The other terminal end of the lamp 122 is connected by wire 126 to the contact member 112 associated with the prong 102. The lamp 122 is a glass neon bulb rated such that it will turn on when connected to 110 volts AC and will withstand instantaneous voltages of at least 550 V AC. The resistor 120 is 470 K$\Omega$ and rated for ¼ W. The lamp 122 is positioned inside the shell 101 so that it is aligned with the translucent window 116 shown in FIG. 1.

FIG. 3 is a perspective view showing how the prior art tester 100 contacts defibrillator electrodes 128 and 130 after the defibrillator's discharge capacitor is indicated as being charged. The electrode 128 has a patient contact surface (dish surface) 132 and the electrode 130 has a patient contact surface (dish surface) 134. The tester 100 and electrodes 128 and 130 are positioned so that the contact member 112 associated with the prong 102 touches the contact surface 132 of the electrode 128 while the contact member 112 associated with the prong 104 touches the contact surface 134 of the electrode 130. If the capacitor is charged, the voltage across the contact members 112 will cause the lamp 122 to glow. The glowing lamp 122 will be visible to an operator through the translucent window 122.

A typical testing routine involves setting the defibrillator to output a relatively small amount of energy, such as about 2–5 joules, and touching the contact members of the tester 100 to the respective contact surfaces of the electrodes 128 and 130. If the lamp 122 glows, the tester 100 is removed, the defibrillator is turned up to its working setting and the electrodes 128, 130 are placed on a patient for discharge. In one type of defibrillator employed today, the working setting is about 100 joules for internal defibrillation and up to about 300 joules for external defibrillation. The testing routine is conducted at much lower energy levels because small defects in the carbon fiber wires connecting the defibrillator to the electrodes are more readily detected at such lower levels. Testing at lower energy levels is also safer. At higher energy levels, the voltage will spark or jump across the electrodes 128, 130 as the tester's contact members are brought in close proximity thereto.

The prior art tester 100 suffers from numerous disadvantages. One disadvantage is that each of the contact members 112 terminate in a pointed end. A pointed end easily scratches electrode contact surfaces. Also, pointed ends make point contact with the electrode contact surfaces. Point contact is disadvantageous because it requires relatively delicate maneuvering to ensure that appropriate contact is made and because it presents a relatively small surface area for contact. Since the tester 100 is usually employed in emergency or highly stressful conditions, the need to employ delicate maneuvering while conducting the test is not desirable. The relatively small contact surface, illustrated in FIGS. 4 and 5, is not desirable in view of the extremely high voltage levels associated with defibrillators. Furthermore, since resistance at the contact area is inversely related to the contact surface area, a small surface area will result in a high resistance. Preferably, resistance at the contact area should be as low as possible.

FIG. 4 shows a bottom perspective view of the prongs 102 and 104 of the prior art tester 100. As clearly shown in this view, the distal ends of the pointed conductive contact members 112 have very little surface area. The contact members 112 in this prior art tester 100 have an outer diameter $d_1$ of about 2 mm. Thus, the maximum surface area of the distal end of the contact member 112 is about $\pi(2 \text{ mm}/2)^2$ or about 3.14 sq. mm. However, since the ends of the contact members 112 are rounded to a point, the actual surface area of the distal end is much less than this value.

FIG. 5 is a sectional view of the prior art tester 100 showing the contact member 112 of the prong 102 in contact with the contact surface 132 of the electrode 128.

Another disadvantage of the prior art tester 100 is that it is reusable. Although reusability would normally be a desirable feature, reusability in this instance creates potential medical problems. It is essential that the tester 100 be properly sterilized before use. Accordingly, the tester 100 is sterilized by the supplier and shipped in sealed plastic wrappers which are removed immediately before use. After use, the tester 100 is obviously not sterilized anymore. Furthermore, if the same patient is given repeated shocks, the tester 100 will touch electrodes which have directly contacted the patient, assuming that the same tester 100 is used with each patient episode. Thus, the tester 100 could potentially harbor infectious matter which might contaminate the next patient if the same tester 100 is reused. Currently, there is no fail-safe way to ensure that medical facilities do not reuse the tester 100.

Thus, there is still a need for a defibrillator charge tester which is easy to maneuver, which makes improved contact with electrodes and which cannot be inadvertently reused. The present invention fills that need.

SUMMARY OF THE INVENTION

The present invention provides a defibrillator charge tester for contacting two defibrillator electrode surfaces comprising a generally Y-shaped nonconductive shell and a charge testing circuit. The shell has two distal ends associated with prongs of the Y-shaped shell and a proximal end for holding the tester. The charge testing circuit is disposed in the shell. The circuit has two conductive terminal ends. Each terminal end extends through the shell at a respective distal end of one of the prongs and terminates in a conductive circular plate-shaped contact member. The contact member contacts a respective one of the two defibrillator electrode surfaces.

In another embodiment of the invention, the circuit includes a fuse for breaking the circuit's continuity when current through the fuse exceeds a given value, thereby preventing reuse of the tester.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DESCRIPTION OF THE PREFERRED EMBODIMENT

Figure 1:
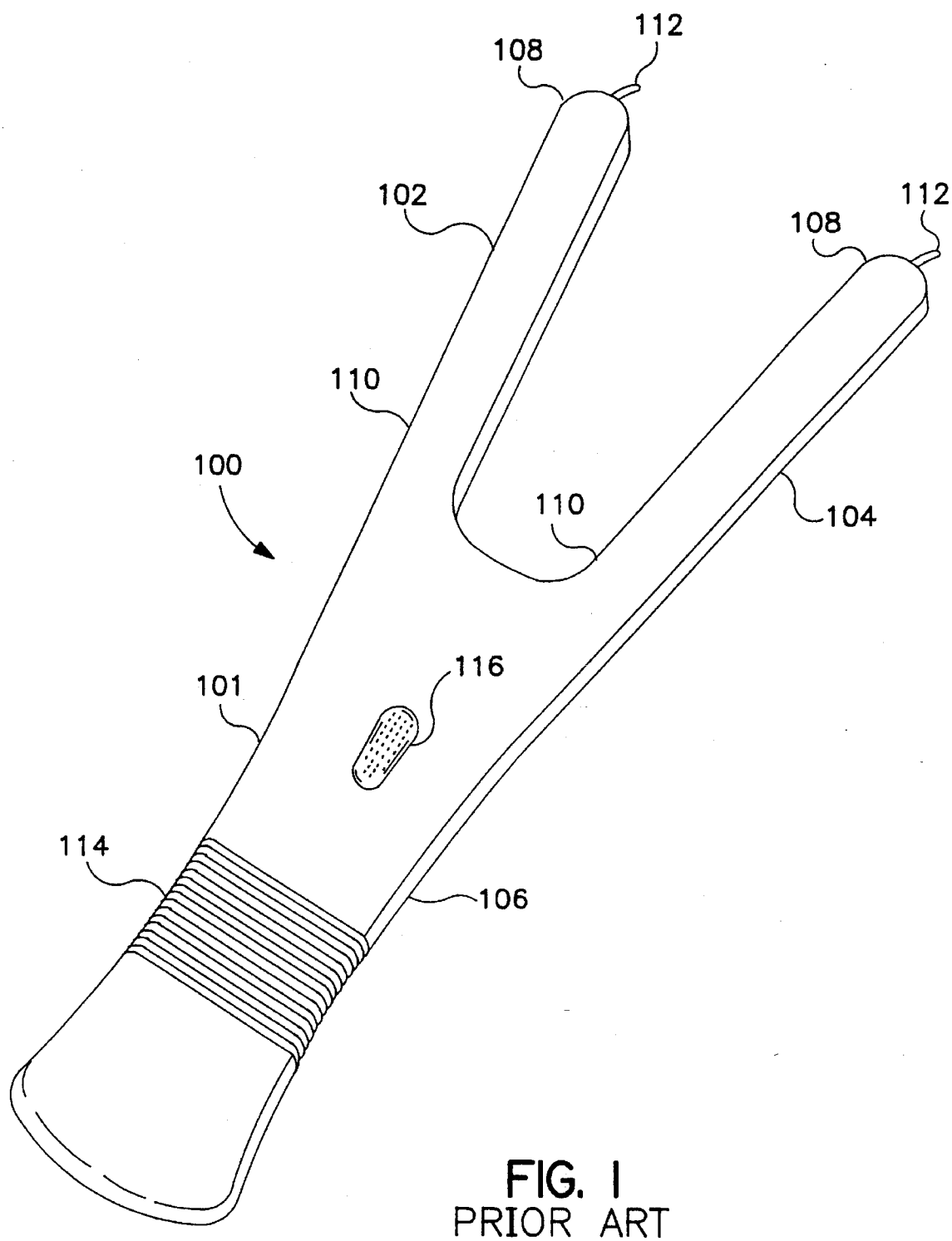
FIG. 1 is a top perspective view of a prior art tester.
Figure 2:
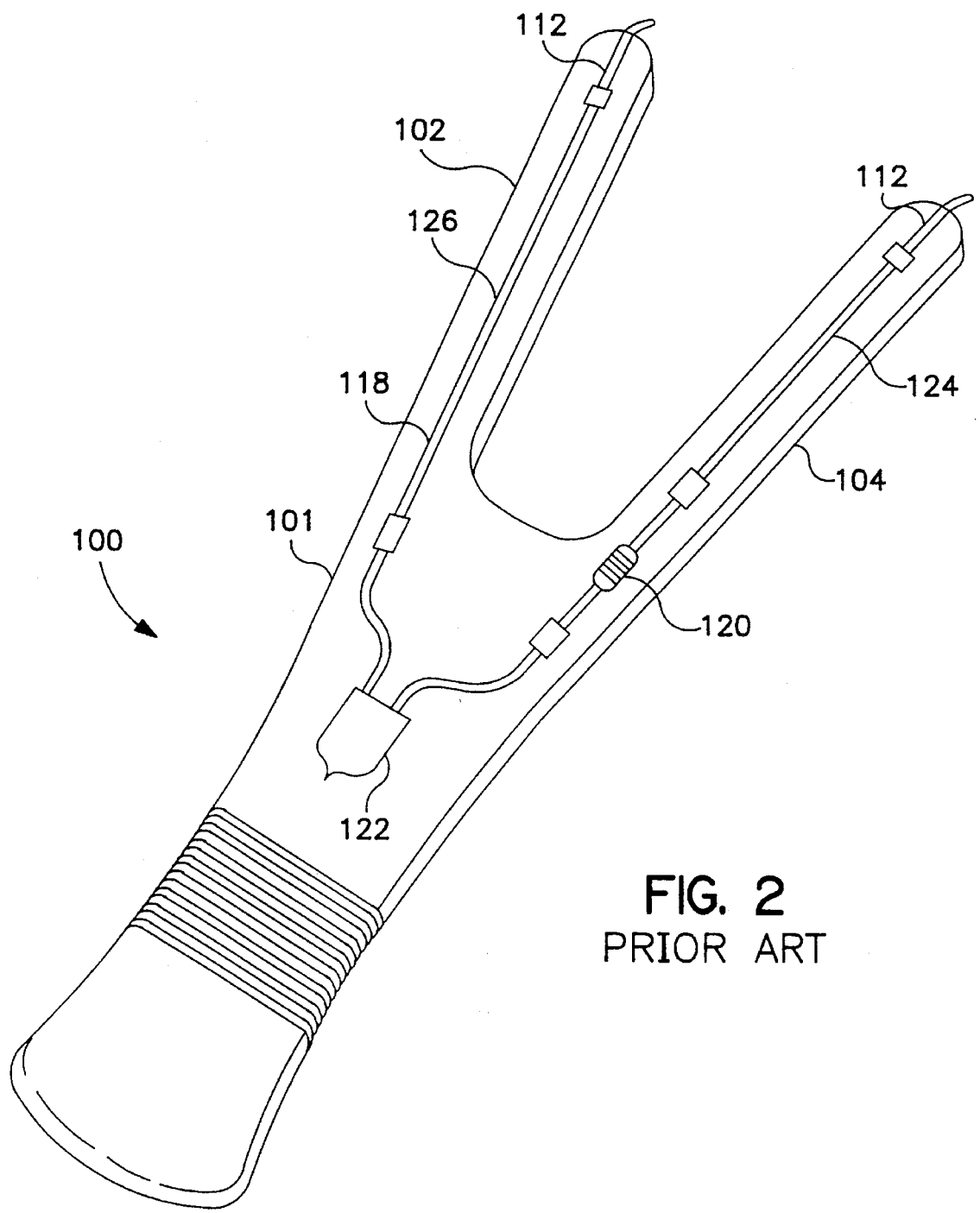
FIG. 2 shows the charge testing circuit disposed inside the prior art tester of FIG. 1.

While the invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

Apparatus depicting the preferred embodiments of the novel defibrillator charge tester are illustrated in the drawings.

Figure 6:
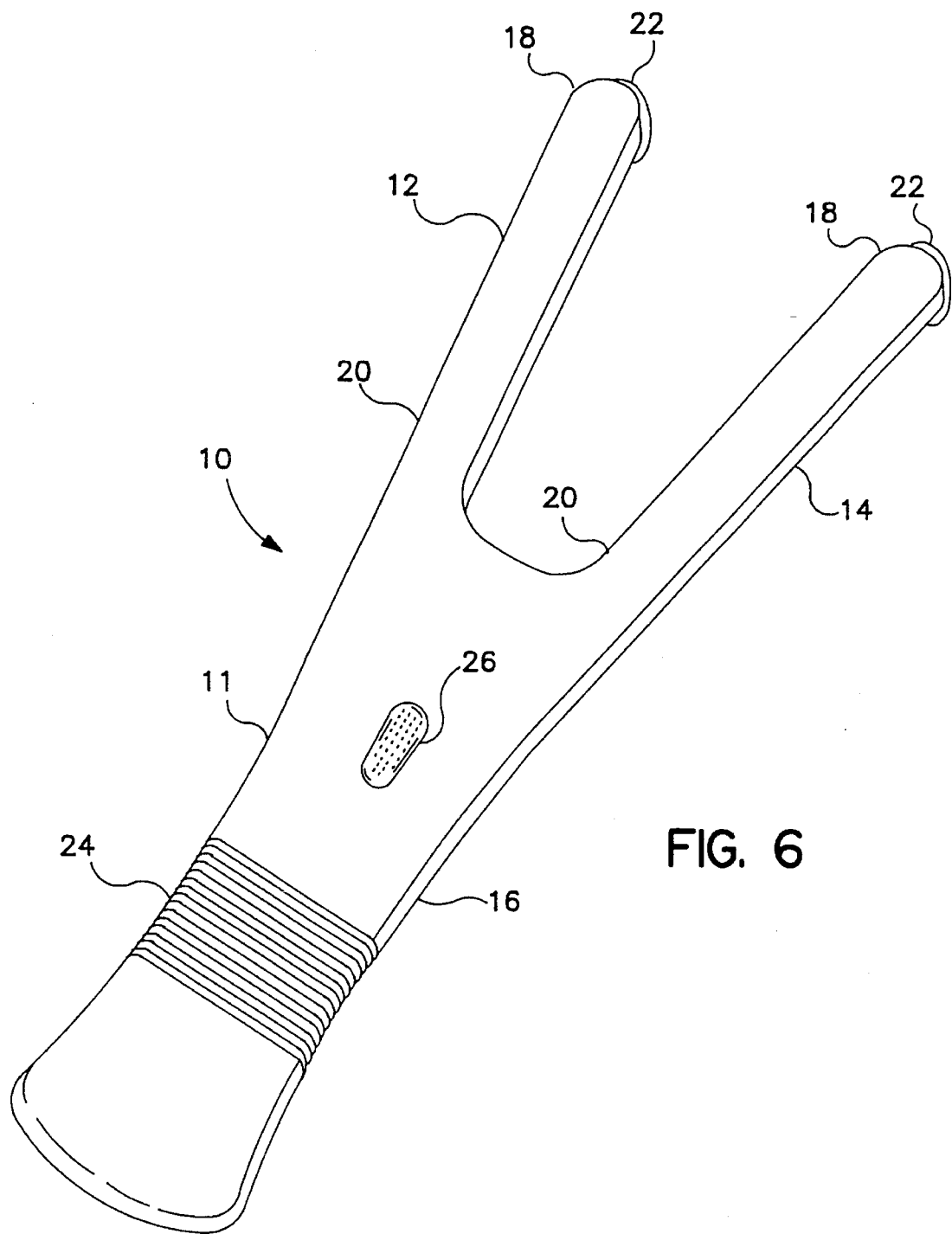
FIG. 6 is a top perspective view of a defibrillator charge tester according to a preferred embodiment of the present invention.
Figure 8:
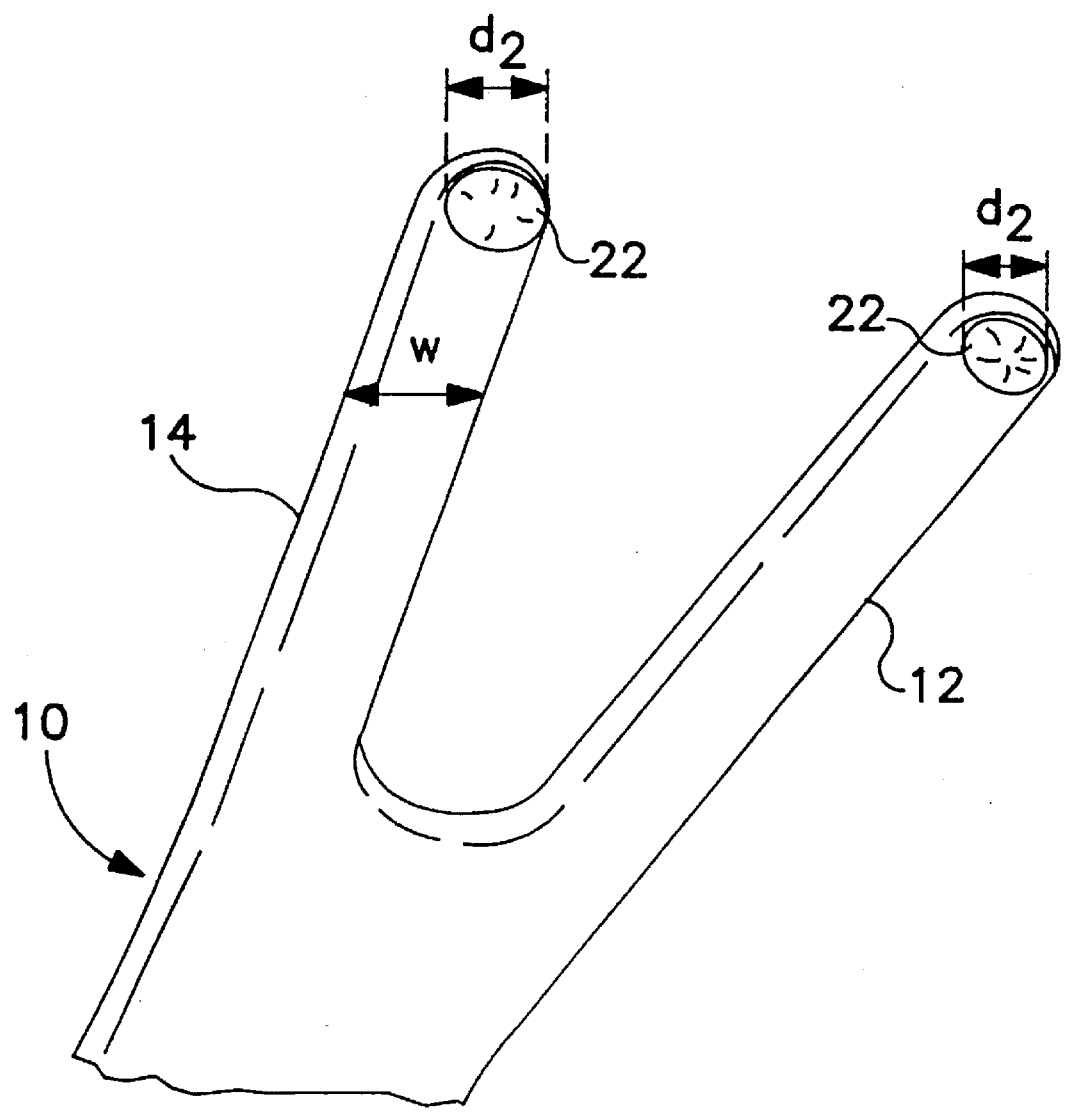
FIG. 8 is a bottom perspective view of the prongs and contact members of the tester of FIG. 6.
Figure 10:
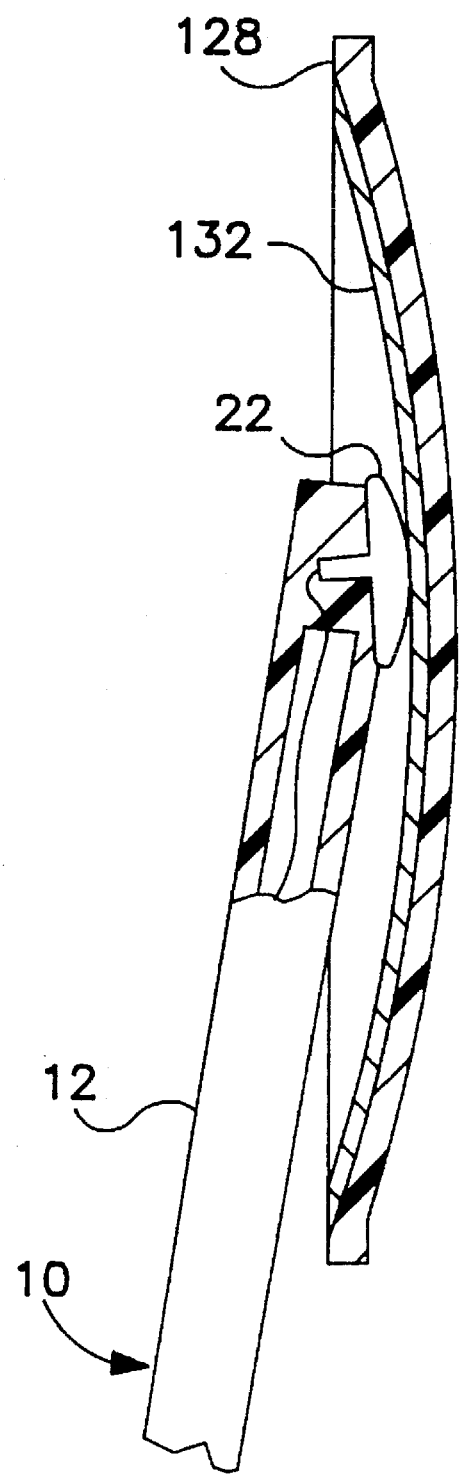
FIG. 10 is a sectional view taken through line 10—10 of FIG. 9 showing a contact member of the tester in contact with an electrode.

FIG. 6 is a top perspective view of the novel tester 10. The tester 10 includes a generally Y-shaped flattened nonconductive hollow plastic shell 11, similar to the shell 101 in the prior art tester 100. Accordingly, the Y-shaped shell 11 is also defined by identical tines or prongs 12 and 14 and a handle portion 16. Each prong 12 and 14 has a rounded distal end 18 and a proximal end 20. The tester 10 does not have a pointed conductive contact member, as provided in the prior art tester 100. Instead, the tester 10 has circular plate-shaped contact members 22 extending from the distal ends 18 of each of the prongs 12 and 14, as best illustrated in FIGS. 8 and 10 described below. The handle portion 16 includes ridges 24 for assisting the operator in gripping the tester 10. The mid-section of the top side of the handle portion 16 has a cut-out covered by a translucent window 26.

Figure 7:
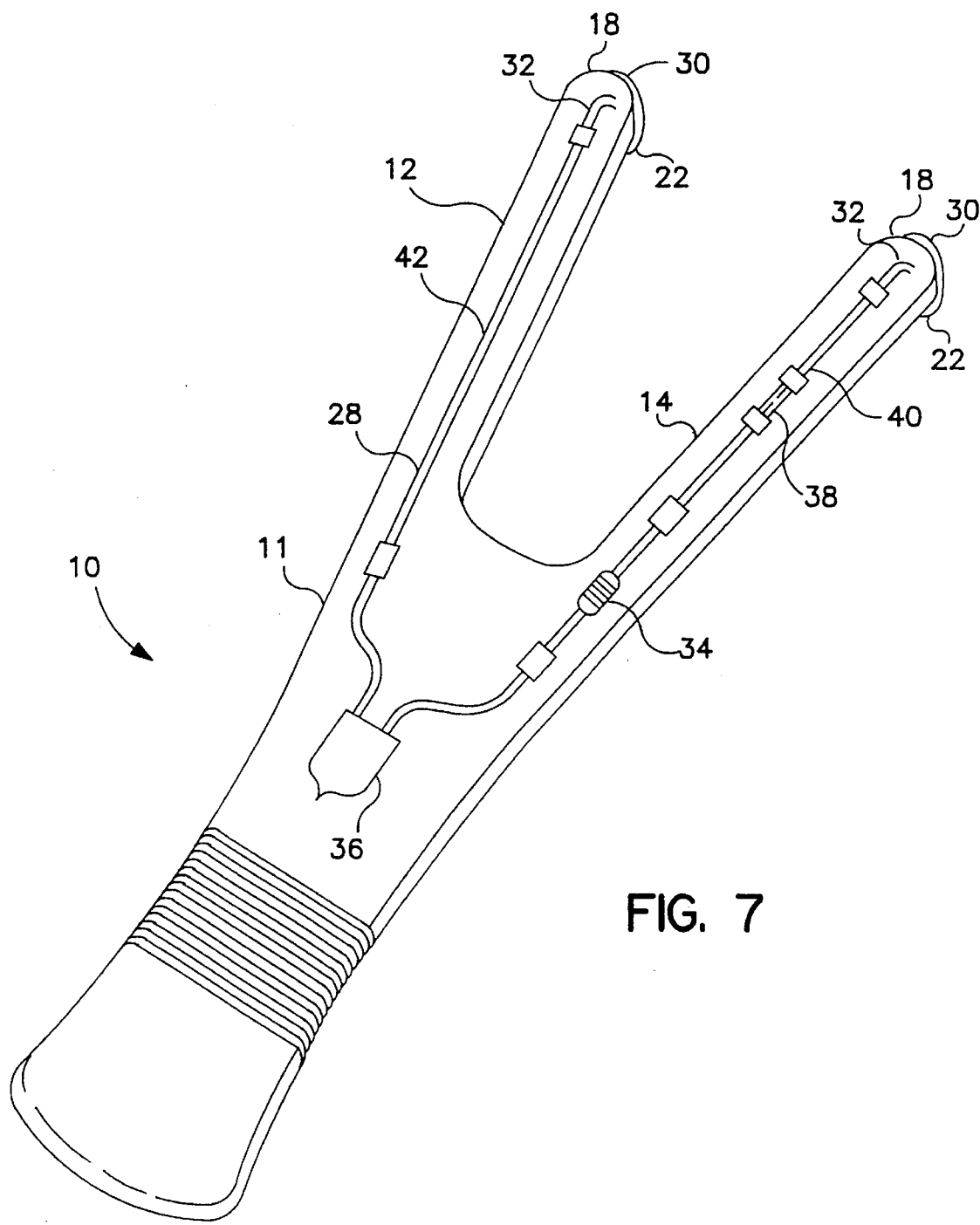
FIG. 7 shows the charge testing circuit disposed inside the tester of FIG. 6.

FIG. 7 shows charge testing circuit 28 superimposed over the tester 10 with the components of the testing circuit 28 in their approximate locations with respect to the parts of the shell 11. It should be understood that all portions of the testing circuit 28, except for the circular plate-shaped portion of the protruding contact members 22, are normally disposed inside the shell 11. That is, the contact members 22 actually extend through the shell 11 and thus terminate inside of the shell 11.

In the preferred embodiment, the contact members 22 have the overall appearance of a thumbtack, best shown in FIG. 8 described below. Thus, each contact member 22 has a circular plate-shaped portion 30 external to the shell 11 and a shaft 32 extending rearward from the inner facing surface of the plate-shaped portion 30 into the shell 11. The shaft 32 connects to a terminal end of the testing circuit 28. In the preferred embodiment, the plate-shaped portion 30 lies flush against the prong's distal end 18. However, in an alternative embodiment, a portion of the shaft 32 extends slightly out of the shell 11 so that the plate shaped portion 30 does not lie flush against the prong's distal end 18, but rather is spaced a short distance therefrom.

The testing circuit 28 is a series connected path comprising the two contact members 22, a resistor 34, a lamp 36 and a fuse 38. One end of the resistor 34 is connected to one end of the fuse 38. The other end of the fuse 38 is connected by wire 40 to the contact member 22 associated with the prong 14. The other end of the resistor 34 is connected to one terminal end of the lamp 36. The other terminal end of the lamp 36 is connected by wire 42 to the contact member 22 associated with the prong 12.

In one embodiment of the invention, the resistor 34 and lamp 36 and are similar in type and ratings to the resistor 120 and lamp 122 in the prior art tester 100. Likewise, the lamp 36 is positioned inside the shell 11 so that it is aligned with the translucent window 26 shown in FIG. 6, in the same manner as in the prior art tester 100.

Unlike the testing circuit 118 in the reusable prior art tester 100, the testing circuit 28 in the tester 10 includes fuse 38 to prevent reuse of the tester 10. The fuse 38 is rated so that it will break the circuit's continuity when current through the fuse 38 exceeds a given value. That value is set to be equal or less than the current through the circuit 28 when the contact members 18 make contact with electrodes of a charged defibrillator. The fuse 38 should be a slow-blowing fuse so that the lamp 36 will glow for a short, noticeable period of time before the circuit continuity is broken by the fuse 38. The testing routine and defibrillator energy levels employed for the tester 10 are similar to the testing routine and defibrillator energy level employed for the prior art tester 100.

FIG. 8 shows a bottom perspective view of the prongs 12 and 14 of the tester 10 and best illustrates the circular plate-shaped contact members 22. As clearly shown in this view, the contact members 22 have significantly greater surface area that the pointed conductive contact members 112 of the prior art tester 100.

In one embodiment of the tester 10 wherein the tester's dimensions are similar to the prior art tester 100, the contact members 22 in the tester 10 have an outer diameter $d_2$ as large as 16.6 mm which is the approximate width w of the prongs 12, 14. However, since the prong's distal ends are rounded, an outer diameter $d_2$ in the range of about 5 mm to about 10 mm will be more appropriate to maintain a smooth overall profile. Thus, the maximum surface area of the outer surface of the circular plate-shaped portion of the contact member 22 will be about $\pi(16.6 \text{ mm}/2)^2$ or about 216 sq. mm. If the outer diameter $d_2$ is about 5 mm to about 10 mm, the surface area will range from about 19.6 sq. mm to about 78.5 sq. mm. Thus, even if the outer diameter is at the low end of this range (e.g., about 5 mm), the surface area will be over six times greater than the maximum 3.14 sq. mm. surface area of the prior art point contact member 112. The greater contacting surface area of the novel tester 10 makes the tester 10 easier to maneuver since precise contact need not be made. Likewise, the greater surface area improves the contact member/electrode contact. One advantage of this improved contact is lower resistance at the contact area. Furthermore, the circular plate-shaped contact member 22 is significantly less prone to scratch the electrode contact surfaces than the pointed contact member 112 in the prior art tester 100.

Figure 3:
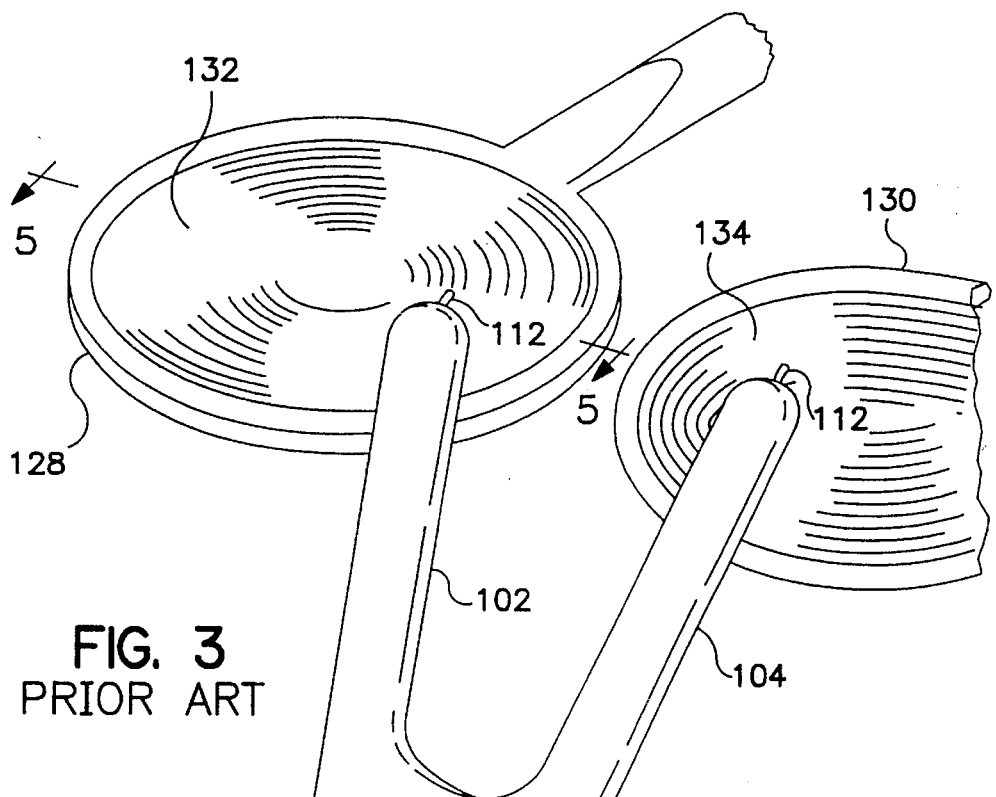
FIG. 3 is a perspective view showing how the prior art tester of FIG. 1 tests defibrillator electrodes.
Figure 4:
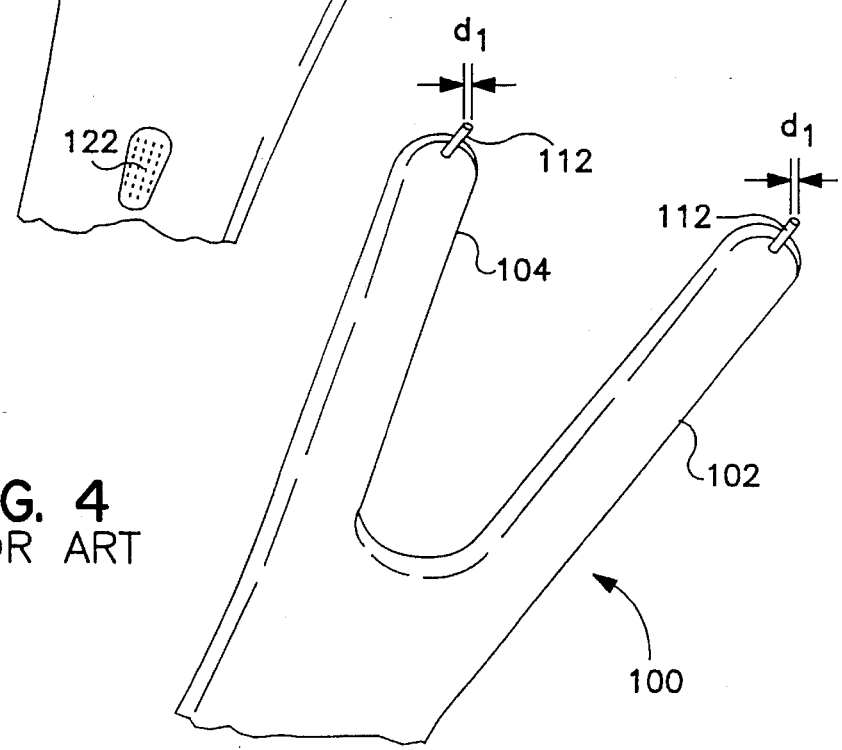
FIG. 4 is a bottom perspective view of the prongs and contact members of the prior art tester of FIG. 1.
Figure 9:
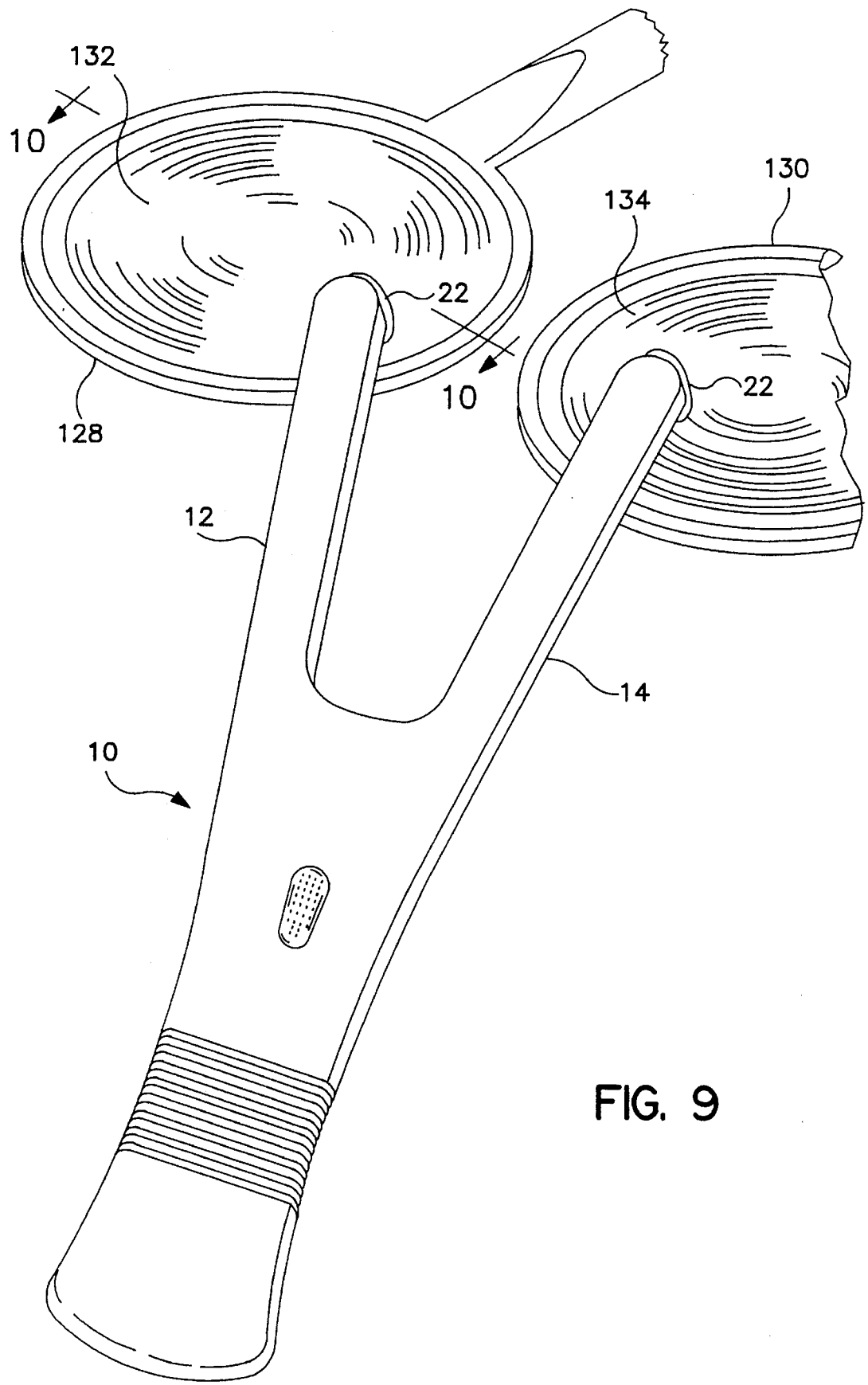
FIG. 9 is a perspective view showing how the tester of FIG. 6 tests defibrillator electrodes.

FIG. 9 is a perspective view showing how the novel tester 10 tests the defibrillator electrodes 128 and 130 described above in FIG. 3. The tester 10 and electrodes 128 and 130 are positioned so that the contact member 22 associated with the prong 12 touches the contact surface 132 of the electrode 128 while the contact member 22 associated with the prong 14 touches the contact surface 134 of the electrode 130. If the defibrillator's capacitor is charged, the voltage across the contact members 22 will cause the lamp 22 to glow for a noticeable, but short period. Subsequently, the fuse 38 (not shown) will blow, rendering the tester 10 unusable.

Figure 5:
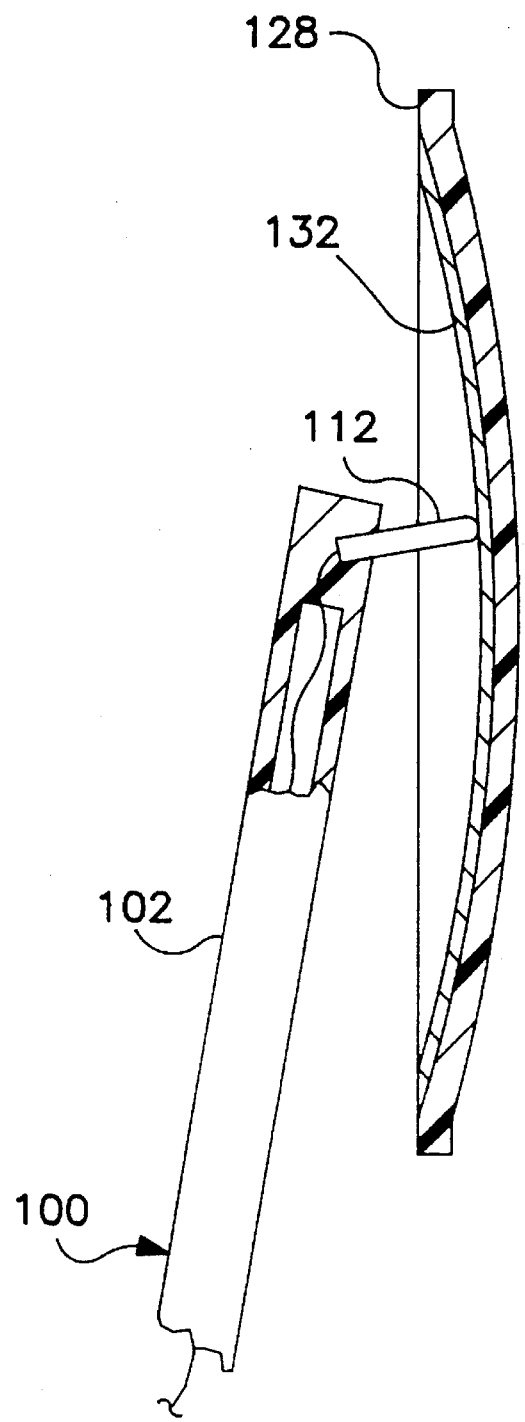
FIG. 5 is a sectional view taken through line 5—5 of FIG. 3 showing a contact member of the prior art tester in contact with an electrode.

FIG. 10 is a sectional view of the tester 10 taken through line 10—10 of FIG. 9 and further illustrates the improved contact member/electrode contact associated with the novel tester 10. FIG. 10 shows the contact member 22 of the prong 12 in contact with the contact surface 132 of the electrode 128. The contact surface area of the tester 10 is significantly greater than the contact surface area of the prior art tester 100 shown in corresponding FIG. 5.

To further improve the contact surface area in the tester 10, the contact members 22 may have a concave outer facing surface, as shown in FIG. 10. This improves the contact surface area when the tester 10 is employed to test an electrode having a convex contact surface, as illustrated in FIG. 10. Although this concavity reduces the contact surface area when the tester 10 is employed to test an electrode having a flat contact surface (e.g., an electrode used on an infant), the contact surface area of the tester 10 will still be significantly greater than the contact surface area of the prior art tester 100 employed with a flat electrode.

Although the invention is disclosed in the context of a Y-shaped shell, other shell shapes which allow for separation of two prongs or tines from a single handle are within the scope of the invention. Thus, the Y-shaped shell is merely one example of a forked type of shell.

The present invention may be embodied in other specific forms without departing from the spirit or essential attributes thereof and, accordingly, reference should be made to the appended claims, rather than to the foregoing specification, as indicating the scope of the invention.

What is claimed is:

1. A defibrillator charge tester for detecting the presence of an electrical charge on the electrode surfaces of a defibrillator, said charge tester comprising:
   (a) a generally fork-shaped nonconductive shell with two prongs, the shell having two distal ends associated with the prongs and a proximal end for holding the tester; and
   (b) a charge testing circuit disposed in the shell, the circuit having two conductive terminal ends, each terminal end extending through the shell at a respective distal end of one of the prongs and terminating in a conductive plate-shaped contact member for contacting a respective one of the two defibrillator electrode surfaces, said contact member having a surface area of at least about 19.6 sq. mm.

2. A defibrillator charge tester according to claim 1 wherein the circuit includes a lamp for visually indicating that current is flowing through the circuit, the circuit allowing the lamp to glow only when the current flowing through the circuit exceeds a first predetermined value.

3. A defibrillator charge tester according to claim 2 wherein the circuit also includes a fuse for breaking the circuit's continuity when current through the fuse exceeds the first predetermined value.

4. A defibrillator charge tester according to claim 3 wherein the fuse is a slow-blowing fuse to allow the lamp to glow for a short period of time before the circuit continuity is broken.

5. A defibrillator charge tester according to claim 1 wherein the contact member has a concave outer facing surface.

6. A defibrillator charge tester according to claim 1 wherein the contact member is flush against the distal end of the prong.

7. A defibrillator charge tester according to claim 1 wherein the circuit includes a fuse for breaking the circuit's continuity when current through the fuse exceeds a given value.

8. A defibrillator charge tester according to claim 1 wherein the circuit includes a lamp for visually indicating that current is flowing through the circuit.

9. A defibrillator charge tester according to claim 1 wherein the shell is generally Y-shaped.

10. A defibrillator charge tester according to claim 1 wherein the contact member is circular.

11. A defibrillator charge tester for detecting the presence of an electrical charge on the electrode surfaces of a defibrillator, said charge tester comprising:

a generally Y-shaped nonconductive shell having a handle portion and a plurality of elongated portions extending from one end of the handle portion;

a charge testing circuit disposed in the shell, the circuit comprising (i) a plurality of conductive terminal ends, each terminal end extending through the shell at a respective distal end of one of the elongated portions and terminating in a conductive contact member for contacting a respective defibrillator electrode surface, (ii) an indicator electrically connected to the terminal ends for indicating that current is flowing through the circuit, said indicator being activated when the current flowing through the circuit exceeds a first predetermined value, and (iii) a slow-burning fuse electrically connected to the terminal ends for breaking the continuity of the circuit when current passing through the fuse exceeds the first predetermined value and for permitting the activation of the indicator for a short period of time before the circuit continuity is broken.

12. A defibrillator charge tester according to claim 11 wherein the indicator is a lamp.

13. A defibrillator charge tester according to claim 11 wherein the contact member is an enlarged member having a surface area of at least about 19.6 sq. mm.

14. A defibrillator charge tester according to claim 11 wherein the contact member has a circular shape.

15. A defibrillator charge tester for contacting two defibrillator electrode surfaces comprising:

(a) a generally fork-shaped nonconductive shell with two prongs, the shell having two distal ends associated with the prongs and a proximal end for holding the tester; and (b) a charge testing circuit disposed in the shell, the circuit comprising two conductive terminal ends, each terminal end extending through the shell at a respective distal end of one of the prongs and terminating in a conductive plate-shaped contact member for contacting a respective one of the two defibrillator electrode surfaces; a lamp electrically connected to the terminal ends for visually indicating that current is flowing through the circuit, the circuit allowing the lamp to glow only when the current flowing through the circuit exceeds a first predetermined value; and a slow-blowing fuse electrically connected to the terminal ends for breaking the circuit's continuity when current through the fuse exceeds the first predetermined value, the fuse allowing the lamp to glow for a short period of time before the circuit continuity is broken.

* * * * *